United States Patent
Roeder (10) Patent No.: US 9,545,324 B2
(45) Date of Patent: Jan. 17, 2017

(54) PRE-LOADED ILIAC BRANCH DEVICE AND METHODS OF DEPLOYMENT

(71) Applicant: COOK MEDICAL TECHNOLOGIES LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 981 days.

(21) Appl. No.: 13/799,881

(22) Filed: Mar. 13, 2013

(65) Prior Publication Data

US 2014/0277330 A1    Sep. 18, 2014

(51) Int. Cl.
    *A61F 2/954*    (2013.01)
    *A61F 2/966*    (2013.01)
    *A61F 2/06*    (2013.01)

(52) U.S. Cl.
    CPC .............. *A61F 2/966* (2013.01); *A61F 2/954* (2013.01); *A61F 2002/067* (2013.01); *A61F 2002/9665* (2013.01)

(58) Field of Classification Search
CPC ............ A61F 2/95; A61F 2/954; A61F 2/962; A61F 2/966; A61F 2/97; A61F 2002/9517; A61F 2002/9522; A61F 2002/9665
See application file for complete search history.

(56) References Cited

U.S. PATENT DOCUMENTS

| | | | |
|---|---|---|---|
| 6,261,316 B1 * | 7/2001 | Shaolian | A61F 2/07 604/284 |
| 6,440,161 B1 * | 8/2002 | Madrid | A61F 2/90 606/108 |
| 6,660,030 B2 * | 12/2003 | Shaolian | A61F 2/07 623/1.11 |
| 6,663,665 B2 * | 12/2003 | Shaolian | A61F 2/07 623/1.35 |
| 6,689,157 B2 * | 2/2004 | Madrid | A61F 2/90 606/108 |
| 6,695,875 B2 | 2/2004 | Stelter et al. | |
| 6,939,370 B2 | 9/2005 | Hartley et al. | |
| 6,953,475 B2 * | 10/2005 | Shaolian | A61F 2/07 623/1.11 |
| 6,974,471 B2 | 12/2005 | Van Schie et al. | |
| 7,108,715 B2 | 9/2006 | Lawrence-Brown et al. | |
| 7,175,652 B2 | 2/2007 | Cook et al. | |
| 7,232,459 B2 | 6/2007 | Greenberg et al. | |
| 7,294,147 B2 | 11/2007 | Hartley | |

(Continued)

FOREIGN PATENT DOCUMENTS

| | | |
|---|---|---|
| EP | 1920734 A2 | 5/2008 |
| EP | 2417942 A1 | 2/2012 |

(Continued)

OTHER PUBLICATIONS

European Search Report for EP 14275045 dated Sep. 16, 2014 (7 pages).

*Primary Examiner* — Ryan J Severson
(74) *Attorney, Agent, or Firm* — Brinks Gilson & Lione (57) ABSTRACT

Methods for accessing the common and internal iliac arteries and delivering and deploying an endovascular graft therein utilizing an ipsilateral approach are disclosed. A system including a pre-loaded delivery and deployment device to enable such a method to be practiced is also disclosed.

25 Claims, 10 Drawing Sheets

(56) References Cited

U.S. PATENT DOCUMENTS

| | | |
|---|---|---|
| 7,393,357 B2 | 7/2008 | Stelter et al. |
| 7,435,253 B1 | 10/2008 | Hartley et al. |
| 7,691,135 B2 * | 4/2010 | Shaolian .................... A61F 2/07 606/108 |
| 7,753,918 B2 | 7/2010 | Hartley et al. |
| 7,780,717 B2 | 8/2010 | Ducke et al. |
| 7,803,177 B2 | 9/2010 | Hartley et al. |
| 7,815,608 B2 | 10/2010 | Schafersman et al. |
| 7,846,194 B2 | 12/2010 | Hartley et al. |
| 7,867,270 B2 | 1/2011 | Hartley et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,114,145 B2 | 2/2012 | Hartley et al. |
| 8,147,535 B2 * | 4/2012 | Shaolian .................... A61F 2/07 623/1.11 |
| 8,167,925 B2 * | 5/2012 | Shaolian .................... A61F 2/07 606/108 |
| 8,167,930 B2 | 5/2012 | Allen et al. |
| 8,172,895 B2 | 5/2012 | Anderson et al. |
| 8,262,718 B2 | 9/2012 | Chuter et al. |
| 8,357,190 B2 | 1/2013 | Fearn et al. |
| 8,394,136 B2 | 3/2013 | Hartley et al. |
| 8,449,600 B2 | 5/2013 | Hartley et al. |
| 8,480,726 B2 | 7/2013 | Cunningham et al. |
| 8,506,616 B2 | 8/2013 | Hartley et al. |
| 8,753,385 B2 * | 6/2014 | Hartley .................... A61F 2/95 623/1.11 |
| 8,845,708 B2 * | 9/2014 | Hartley .................... A61F 2/954 623/1.11 |
| 8,945,200 B1 * | 2/2015 | Eblacas .................... A61F 2/954 623/1.12 |
| 2001/0007954 A1 * | 7/2001 | Shaolian .................... A61F 2/07 623/1.11 |
| 2001/0012943 A1 * | 8/2001 | Shaolian .................... A61F 2/07 606/108 |
| 2002/0049412 A1 * | 4/2002 | Madrid .................... A61F 2/90 604/164.05 |
| 2002/0058905 A1 * | 5/2002 | Madrid .................... A61F 2/90 604/43 |
| 2003/0199967 A1 | 10/2003 | Hartley et al. |
| 2003/0225446 A1 | 12/2003 | Hartley |
| 2004/0064146 A1 * | 4/2004 | Shaolian .................... A61F 2/07 606/108 |
| 2004/0098087 A1 * | 5/2004 | Madrid .................... A61F 2/90 623/1.11 |
| 2004/0138735 A1 * | 7/2004 | Shaolian .................... A61F 2/07 623/1.11 |
| 2006/0020320 A1 * | 1/2006 | Shaolian .................... A61F 2/07 623/1.11 |
| 2006/0095050 A1 | 5/2006 | Hartley et al. |
| 2006/0095118 A1 | 5/2006 | Hartley |
| 2006/0136046 A1 | 6/2006 | Hartley et al. |
| 2007/0019122 A1 | 1/2007 | Lee et al. |
| 2007/0043425 A1 | 2/2007 | Hartley et al. |
| 2007/0123910 A1 | 5/2007 | Hartley et al. |
| 2007/0185558 A1 | 8/2007 | Hartley |
| 2007/0250154 A1 | 10/2007 | Greenberg et al. |
| 2007/0293940 A1 | 12/2007 | Schaeffer et al. |
| 2008/0221656 A1 | 9/2008 | Hartley et al. |
| 2009/0125095 A1 | 5/2009 | Bui et al. |
| 2010/0179638 A1 * | 7/2010 | Shaolian .................... A61F 2/07 623/1.11 |
| 2010/0249899 A1 | 9/2010 | Chuter et al. |
| 2012/0046728 A1 | 2/2012 | Huser et al. |
| 2012/0172968 A1 | 7/2012 | Chuter et al. |
| 2012/0221096 A1 | 8/2012 | Roeder et al. |
| 2012/0290069 A1 | 11/2012 | Ivancev et al. |
| 2013/0030514 A1 | 1/2013 | Kasprzak et al. |
| 2013/0116775 A1 | 5/2013 | Roeder et al. |
| 2013/0123907 A1 | 5/2013 | Roeder et al. |

FOREIGN PATENT DOCUMENTS

| | | |
|---|---|---|
| EP | 2745813 A1 | 6/2014 |
| WO | WO 2004/019823 A1 | 3/2004 |
| WO | WO 2005/037141 A2 | 4/2005 |

* cited by examiner

PRE-LOADED ILIAC BRANCH DEVICE AND METHODS OF DEPLOYMENT

BACKGROUND

This invention relates generally to medical devices and methods of using the same, and more particularly, to an endovascular stent graft and methods for placement and deployment of the graft in the lumen of a branched vessel.

Stent grafts may be inserted into an anatomical vessel or duct for various purposes. For example, stent grafts are used for treatment of vasculature in the human or animal body to bypass a repair or defect in the vasculature or to maintain or restore patency in a formerly blocked or constricted passageway, such as following a balloon angioplasty procedure. For example, a stent graft may extend proximally and/or distally away from a vascular defect, including a diseased portion of an aneurysm, and engage a healthy portion of a vessel wall. In many cases, however, such a damaged or defective portion of the vasculature may include a branch or side vessel such as an internal iliac artery extending from the common iliac artery. Thus, it has been proposed to provide a stent graft having a side branch which, when deployed, is positioned over the opening to the internal iliac artery and then, if desired, another stent graft can be deployed through the side branch into the internal iliac artery to bypass a diseased portion thereof and restore the blood flow path to the internal iliac artery.

Generally, when deploying an endovascular stent graft into a vessel lumen, it is possible to obtain access to such a lumen from one or both ends of the vessel where necessary, thereby facilitating placement of a graft in the desired portion of the lumen. However, the internal iliac artery, which extends from the common iliac artery below the aortic bifurcation, is a blind vessel because there is no practical way of performing a minimally invasive endovascular procedure into that vessel other than by entry from the common iliac artery.

Access to and introduction of a stent graft into the common and/or internal iliac arteries and successful deployment of a stent graft in such vessels may often depend upon a favorable layout of the arteries and, in many cases, access is difficult. One known approach that has been used includes accessing the target location(s) within the vessels by a contralateral or crossover approach. In other words, a guide wire and/or sheath may be first introduced into a common iliac artery and then snared or pulled from the contralateral side so that the wire and/or sheath extends across the aortic bifurcation where it can be positioned proximal to the opening of the internal iliac artery in which treatment or repair is desired. In this way, a pathway is created to facilitate the introduction and deployment of a stent graft to the target location in the contralateral internal iliac artery.

As endovascular techniques become more refined, physicians continue to seek novel alternative approaches to treating diseased vessels, including blind vessels that are difficult to access and traverse. For example, accessing the target location(s) within the internal iliac artery using an ipsilateral approach (as opposed to the contralateral approach) and therefore avoiding the above-described "crossover" manipulation of a guide wire or sheath over the aortic bifurcation is desirable. Accordingly, a method for accessing the internal iliac arteries utilizing an ipsilateral approach and a pre-loaded deployment system to enable such a method to be practiced is described herein.

While this invention will be generally discussed in relation to a stent graft and method of deployment thereof into a common iliac artery where it is necessary to extend a side branch from a main portion or body of the graft into an internal iliac artery, it is also contemplated that the invention is not so limited and may relate to any body or vessel lumen in which such a deployment is necessary or desired.

SUMMARY

The present disclosure provides a system and method for delivering and deploying an endovascular graft into one or more branched vessels using an ipsilateral approach.

In one example, the system comprises a delivery device comprising a pusher catheter having a proximal end portion and a distal end portion and a first, second and third lumen extending at least partially between the proximal and distal end portions. An auxiliary sheath having a proximal end portion and a distal end portion extends longitudinally within the first lumen of the pusher catheter and a guide wire cannula having a proximal end portion and a distal end portion extends longitudinally within the second lumen of the pusher catheter.

The system further preferably comprises a stent graft carried on the delivery device. In one example, the stent graft has a main tubular body of a biocompatible graft material having a proximal end and a distal end defining a main lumen therebetween. A side branch extends from the main tubular body and has a lumen extending therethrough and in fluid communication with the main lumen. Preferably, the stent graft is configured to be deployed into the vasculature of a patient with the main tubular body being located in the common iliac artery and the side branch being directed towards an internal iliac artery of the common iliac artery. An auxiliary guide wire extends proximally within the lumen of the auxiliary sheath and into the distal end of the main tubular body of the stent graft, and further extends distally through at least a portion of the lumen of the side branch and through the third lumen of the pusher catheter.

The system may also preferably include a second delivery device. In one example, the second delivery device comprises a second guide wire cannula having a proximal end portion and a distal end portion and a lumen extending therebetween. A second stent graft is carried on the proximal end portion of the second delivery device. The second stent graft has a tubular body of a biocompatible graft material defining a main lumen and is configured to be deployed into the internal iliac artery. A second sheath is mounted coaxially over and radially outside at least a portion of the second stent graft.

A method for treating a diseased vessel is also described. In one example, the method comprises the steps of introducing a first delivery device into a patient's vasculature, such as a common iliac artery. The delivery device preferably comprises a pusher catheter having a proximal end portion and a distal end portion and at least two lumens extending therebetween; an auxiliary sheath having a proximal end portion and a distal end portion extending longitudinally within one of the at least two lumens of the pusher catheter and a first prosthesis carried on the first delivery device. The first prosthesis has a main tubular body of a biocompatible graft material having a proximal end portion and a distal end portion defining a main lumen therebetween, and a side branch extending from the main tubular body. The side branch has a lumen extending therethrough and is in fluid communication with the main lumen. Preferably, the first prosthesis is configured to be deployed into the vasculature of a patient with the main tubular body being located in the common iliac artery and the side branch being directed towards an internal iliac artery of the common iliac artery. An auxiliary guide wire extends longitudinally in a proximal direction within the lumen of the auxiliary sheath and into the distal end of the main tubular body of the stent graft, the auxiliary guide wire further extending through at least a portion of the lumen of the side branch and extending longitudinally in a distal direction through the other of the at least two lumens of the pusher catheter.

The method also preferably comprises at least partially deploying the first prosthesis in the common iliac artery; introducing a second delivery device ipsilaterally though the lumen of the main tubular body of the first prosthesis and the lumen of the side branch of the first prosthesis, the second delivery device carrying a second prosthesis thereon, the second prosthesis comprising a tubular body defining a lumen; positioning the second prosthesis within the internal iliac artery; and at least partially deploying the second prosthesis in the internal iliac artery.

DETAILED DESCRIPTION

Throughout this specification the terms "proximal" and "proximally" are used for a position or direction towards the patient's heart and the terms "distal" and "distally" are used for a position or direction away the patient's heart. The term "ipsilateral" is used to indicate that the diseased vessel(s) being accessed during a given procedure are on the same side of the body (right or left) as the vascular access device/introducer, while "contralateral" signifies that the vessel(s) of interest are on the opposite side of the body.

The embodiments described below are in connection with systems and methods for the introduction and deployment of an implantable medical device in a vessel, such as endovascular prosthesis, but could also be used for deploying a range of implantable medical devices including, but not limited to, stents, stent grafts, occlusion devices and the like.

Figure 1:
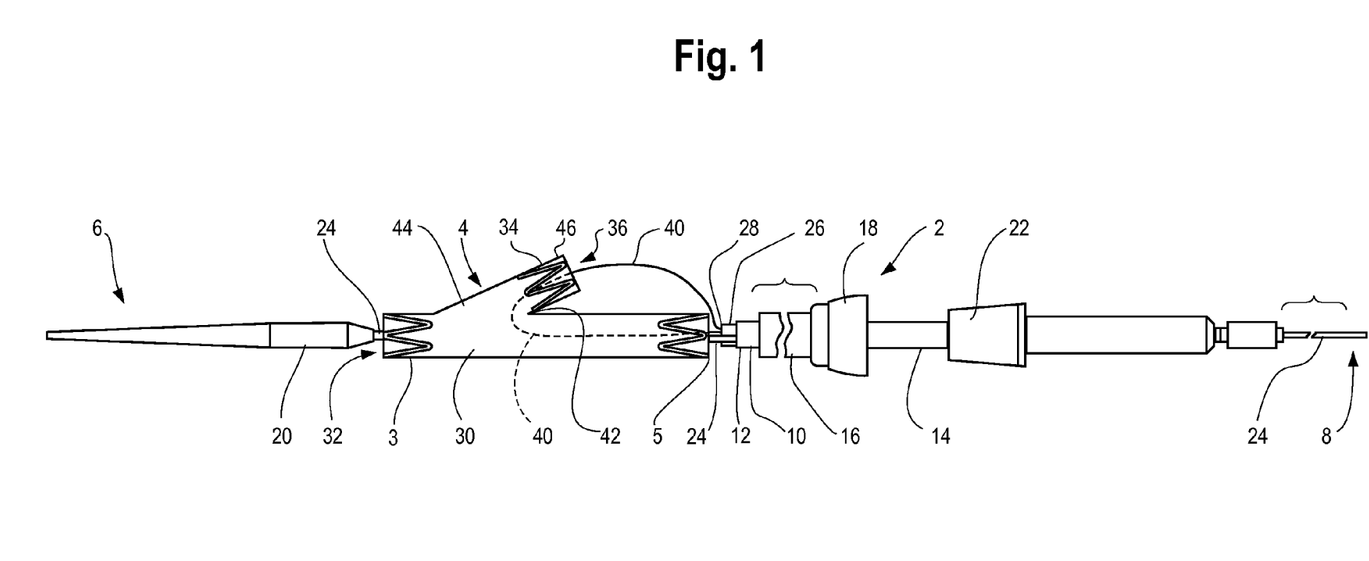
FIG. 1 shows a side view of one example of a pre-loaded delivery and deployment system with a stent graft mounted thereon.

Referring to FIG. 1, an example of a stent graft delivery device, also referred to herein as an "introducer", is shown generally at 2 with a stent graft 4 mounted onto it. During the medical procedure to position and deploy the stent graft, the proximal end 6 of the device 2 will travel through the vessel lumen to a desired deployment site. The distal external manipulation section 8 which may include a handle portion, which is acted upon by a user to manipulate the device, remains outside of the patient throughout the procedure. The delivery device 2 is preferably "pre-loaded", or in other words, before the delivery device is introduced into the patient's vasculature, it is pre-assembled with mechanisms that facilitate graft delivery and deployment already arranged thereon. The delivery and deployment mechanisms may include, for example, one or more guide wires, catheters, sheaths, stent grafts and combinations thereof, which are arranged on and/or are carried by the device 2.

In one non-limiting example, the pre-loaded device 2 preferably includes a mechanism, such as one or more catheters, sheaths and/or guide wires, which extend from a distal external manipulation portion 8 to a proximal end portion 6 where the stent graft 4 is carried. The pre-loaded guide wire(s), catheter(s) and/or sheath(s) remain in place during delivery of the stent graft 4 into a patient's vasculature and aid in placement and deployment of one or more additional or side branch extension stent grafts in a desired location in accordance with the systems and methods described herein.

More specifically, as shown in FIG. 1, the device 2 includes a pusher catheter 10 having a proximal end portion 12 and a distal end portion 14. In one example, the pusher catheter 10 has at least one, but preferably, more than one lumen extending between the proximal 12 and distal 14 end portions. For example, the pusher catheter 10 may have three separate lumens extending longitudinally at least partially between the proximal and distal end portions 12, 14 of the pusher catheter. A sleeve or sheath 16, which may be operated by a sheath manipulator 18, is preferably mounted co-axially over the pusher catheter 10. In the ready-to-deploy position, the sheath 16 extends proximally to the nose cone dilator 20 and covers a stent graft 4 carried on the device 2. As illustrated in FIG. 1, however, the sheath 16 is withdrawn so that the stent graft 4 is exposed to show detail of the assembly. A handle 22 at the distal end 14 of the pusher catheter 10 enables manipulation of various components of the device 2.

As shown in FIG. 1, a guide wire cannula 24 extends through one of the lumens of the pusher catheter 10, from the distal end 8 of the device to immediately distal of the nose cone dilator 20. A branched stent graft 4 may be retained on the device 2, and, in one example, the proximal end of the graft 3 may be secured to the guide wire cannula 24, by a retention arrangement (see FIGS. 12 and 13 for one example of a proximal retention arrangement) immediately distal of the nose cone dilator 20. The branched stent graft 4 may also be retained at its distal end 5 by another retention arrangement (see FIGS. 14 and 15 for examples of a distal retention arrangement) on the device 2.

Figure 2:
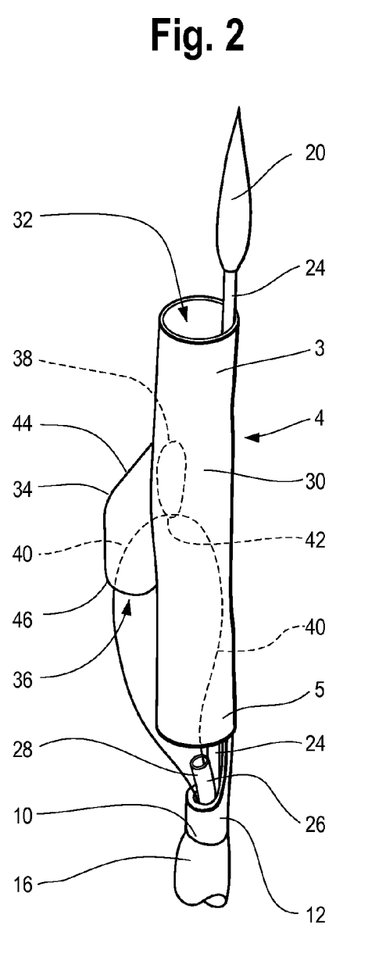
FIG. 2 is a perspective view of one example of the proximal end portion of a pre-loaded delivery device with a stent graft mounted thereon.
Figure 4:
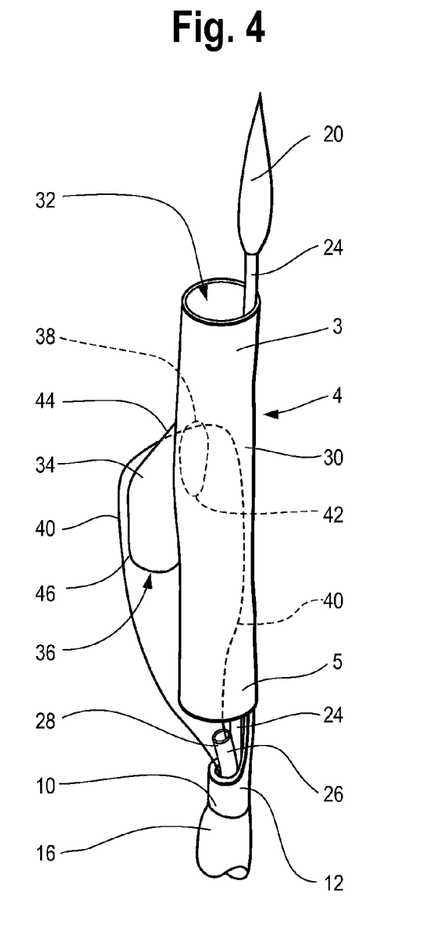
FIG. 4 is a perspective view of another example of the proximal end portion of a pre-loaded delivery device with a stent graft mounted thereon.

As shown in FIGS. 2 and 4, an auxiliary sheath 26 preferably extends through another of the multiple (e.g. three) lumens of the pusher catheter 10 and exits from the pusher catheter 10 (in the pre-deployment state) so that the proximal end or tip 28 of the auxiliary sheath 26 is adjacent the distal end 5 of the branched stent graft 4. The stent graft 4 carried on the device 2 preferably has a substantially tubular main body 30 having a proximal end portion 3 and a distal end portion 5 with a main lumen 32 extending through the main tubular body 30. A side branch 34, also preferably having a substantially tubular body defining a lumen 36, preferably extends from the main body 30 and may be integrally formed with the main body, or alternatively, the side branch 34 may be a separately formed component that is secured to the main body 30 such as by stitching, bonding, adhesive or the like. In either case, the side branch 34 is preferably formed with and/or secured to the main body 30 adjacent a fenestration 38 or opening in the main body 30 so as provide fluid communication between the lumen 32 of the main body and the lumen 36 of the side branch. In one example, both the main body 30 and the side branch 34 are preferably comprised of one or more biocompatible materials including, but not limited to, polyesters, fluorinated polymers and polyurethanes and/or may be made from natural or organic materials. The materials may also be subjected to surface modifications or coatings.

In a preferred example, the stent graft 4 is configured to be deployed into the vasculature of a patient with the main tubular body 30 being located in the common iliac artery and the side branch being directed towards an internal iliac artery of the common iliac artery, although other stent graft configurations for deployment into various other body vessels are also contemplated depending on various factors including, but not limited to the particular vessel(s) being treated and/or the location of a particular damaged or diseased portion of a vessel.

Turning to FIGS. 2-5, within the auxiliary sheath 26 there is an auxiliary guide wire 40 extending therethrough. This auxiliary guide wire 40 extends beyond the proximal tip 28 of the auxiliary sheath 26 and through the lumen 32 of the graft main body 30 and at least partially through the lumen 36 of the side branch 34. For example, a pre-loaded delivery device which has particular application in the delivery and deployment of a stent graft into the internal iliac artery is shown in exemplary FIGS. 2-5. In a first "pre-deployment" position, the auxiliary guide wire 40 extends proximally beyond the distal tip 28 of the auxiliary sheath 26. The auxiliary guide wire 40 enters the main lumen 32 of the stent graft 4 through the graft distal end 5. The auxiliary guide wire 40 then bends in a "U-turn" fashion over the graft bifurcation 42 to enter the side branch 34. The auxiliary guide wire 40 thus enters the lumen 36 of the side branch through a proximal end portion 44 of the branch 34, and hence, it passes through a portion of the main lumen 32 of the stent graft 4 before it bends and enters the lumen 36 of the side branch 34.

Figure 3:
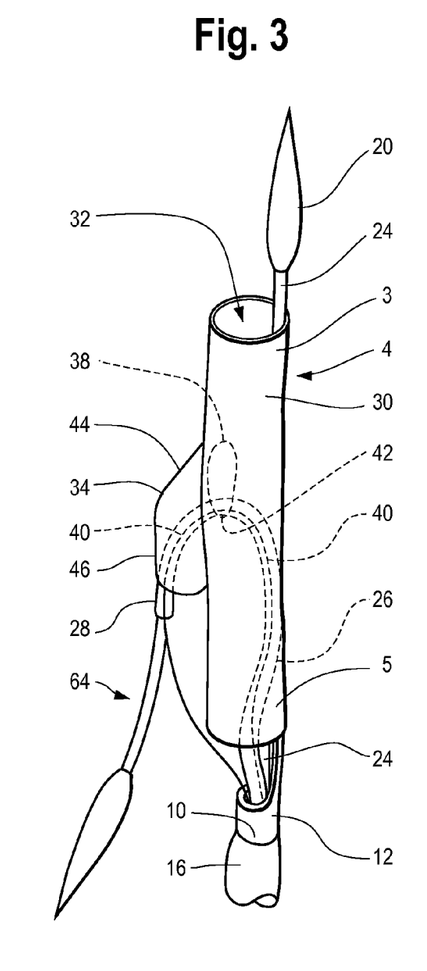
FIG. 3 is a perspective view of the pre-loaded delivery device shown in FIG. 2 with a further delivery device carrying a leg extension stent graft extending through the side branch lumen and positioned for insertion into an internal iliac artery.

In one example of the pre-loaded delivery device 2 as shown in FIGS. 2 and 3, the auxiliary guide wire 40 extends through the entire longitudinal length of the side branch lumen 36 before exiting the branch at distal end 46 and continuing distally along the outside of the main body 30 of the stent graft 4. The auxiliary wire 40 then re-enters a separate or third lumen of pusher catheter 10 (the first and second lumens of the pusher catheter having the auxiliary sheath 26 and the guide wire cannula 24, respectively, extending longitudinally therethough as described above), and the auxiliary guide wire 40 runs distally through the third lumen, back towards the distal end 8 of the device 2.

Figure 5:
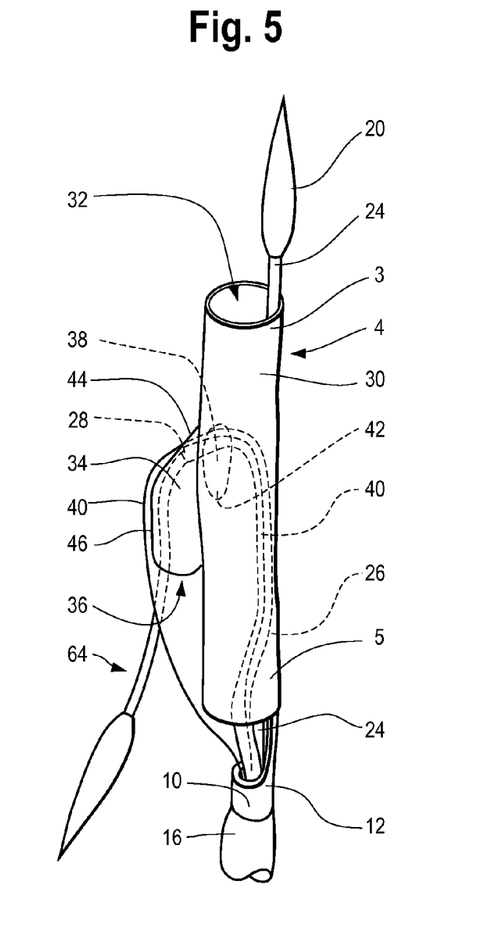
FIG. 5 is a perspective view of the pre-loaded delivery device shown in FIG. 4 with a further delivery device carrying a leg extension stent graft extending through the side branch lumen and positioned for insertion into an internal iliac artery.

An alternative example of a pre-loaded delivery device is illustrated in FIGS. 4 and 5. The same reference numerals are used for corresponding features to those of FIGS. 2 and 3. Like FIG. 2, the auxiliary wire 40 enters the main lumen 32 of the stent graft 4 through the graft distal end 5. The auxiliary wire 40 then extends partially into the proximal end portion 44 of the side branch lumen 36 and then pierces through the graft material near the proximal end portion 44 of the side branch 34. The auxiliary wire 40 then continues in a generally distal direction along the outside of the side branch 34 and main graft body 30, where it preferably re-enters the third lumen of pusher catheter 10 and extends back towards the distal end of the device 8.

Thus, FIGS. 2 through 5 and show several non-limiting examples of a device 2 with a stent graft 4 carried thereon that has been "pre-loaded" with a delivery and deployment mechanism that includes the auxiliary guide wire 40 running through the auxiliary sheath 26 and pusher catheter 10, respectively, through the stent graft lumen 32 and back though a separate lumen of the pusher catheter 10 to the distal end of the device 8.

As illustrated in FIGS. 3 and 5, the auxiliary sheath 26 may be advanced over the auxiliary wire 40 through the main lumen 32 of the graft and at least partially advanced into the proximal end portion 44 of the side branch lumen 36. More specifically, in one example, the auxiliary sheath 26 may be advanced from the first "pre-deployment" position described above and shown in FIG. 2 (in which the proximal end portion 28 of the sheath 26 is located distally of the distal end 5 of the graft) to a second position shown in FIG. 3 in which the sheath 26 has been advanced proximally over the auxiliary wire 40 though the main body lumen 32 and then generally distally though the side branch lumen 36, such that the tip 28 of the auxiliary sheath 26 has exited the distal end 46 of the side branch lumen 36. As such, if the main graft body 30 were located in the lumen of a common iliac artery in the arrangement shown in FIG. 3, the auxiliary sheath 26 would preferably be positioned or directed towards an internal iliac artery of the common iliac artery.

In another alternative example, as illustrated in FIG. 5, the auxiliary sheath 26 can also be advanced over the auxiliary wire 40 though the main body lumen 32. However, the sheath 26 can only be tracked over the wire 40 and extend partially into the proximal end portion 44 of the side branch lumen 36, until the tip 28 of the sheath abuts the interior surface of the side branch lumen 36 adjacent to the point where the auxiliary guide wire 40 pierces though the wall and exits the side branch lumen 36.

Now looking at FIGS. 6 through 11, it will be seen that there is schematically illustrated a series of vessels within the human body, including the common iliac arteries 48 and 50 and the respective internal iliac arteries 52 and 54. The systems and methods described herein find particular application in the delivery, placement and deployment of one or more stent grafts therein, although as discussed earlier, the disclosed systems and methods are not restricted to this particular purpose and may be used in a variety of applications as will be appreciated by one of skill in the art.

Figure 6:
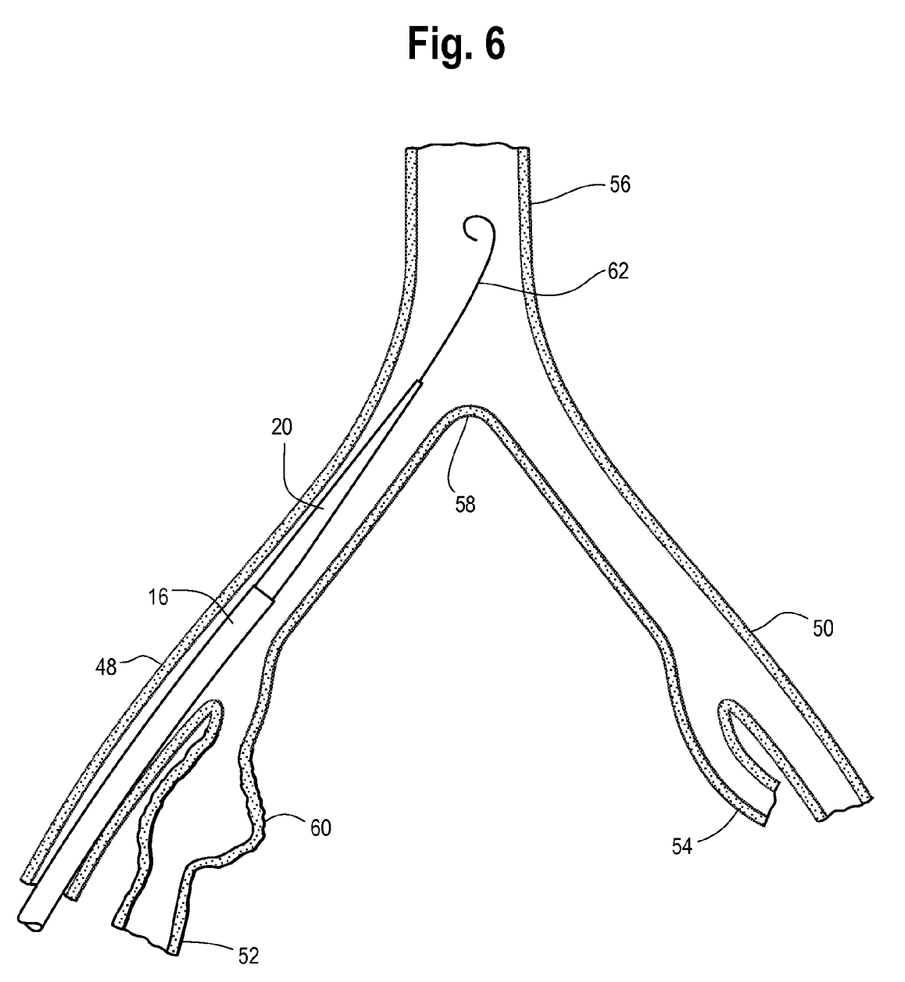
FIGS. 6-11 show an example of the various stages of the introduction, placement and deployment of a stent graft into a common iliac artery and an internal iliac artery using an ipsilateral approach.

Turning to FIG. 6, a descending aorta 56 extends down to an aortic bifurcation 58 from which extend common iliac arteries 48 and 50. From each of the common iliac arteries an internal iliac artery 52 and 54, respectively, extends. In most cases, the internal iliac arteries 52 and 54 cannot be practically accessed from their distal ends remote from the junction with the common iliac artery. For illustrative purposes, internal iliac artery 52 is shown as having a diseased portion, including an aneurysm 60 in FIGS. 6 through 11, although, it will be appreciated that one or both common iliac arteries 48, 50 and/or one or both internal iliac arteries 52, 54 may also include diseased portions that may be treated in accordance with the systems and methods described herein.

As shown in FIG. 6, a guide wire 62 has been extended into a femoral artery via a femoral incision (not shown) and extended proximally beyond the aortic bifurcation 58 to the descending aorta 56. The device 2 has then been introduced into the common iliac artery 48 over the guide wire 56 with the nose cone dilator 20 extending nearly up to the aortic bifurcation 58. Preferably, the delivery device 2 as described herein carries a stent graft 4 thereon that has been "preloaded" with a delivery and deployment mechanism. At this stage, a sheath 16, extending proximally up to the nose cone dilator 20 covers the branched stent graft 4 that is carried on the device 2, so that the stent graft 4 is not visible in FIG. 6. With the device 2 in this position within the lumen of common iliac artery 48, the stent graft 4 (enclosed within the sheath 16) is preferably adjacent to the opening of the internal iliac artery 52.

Figure 7:
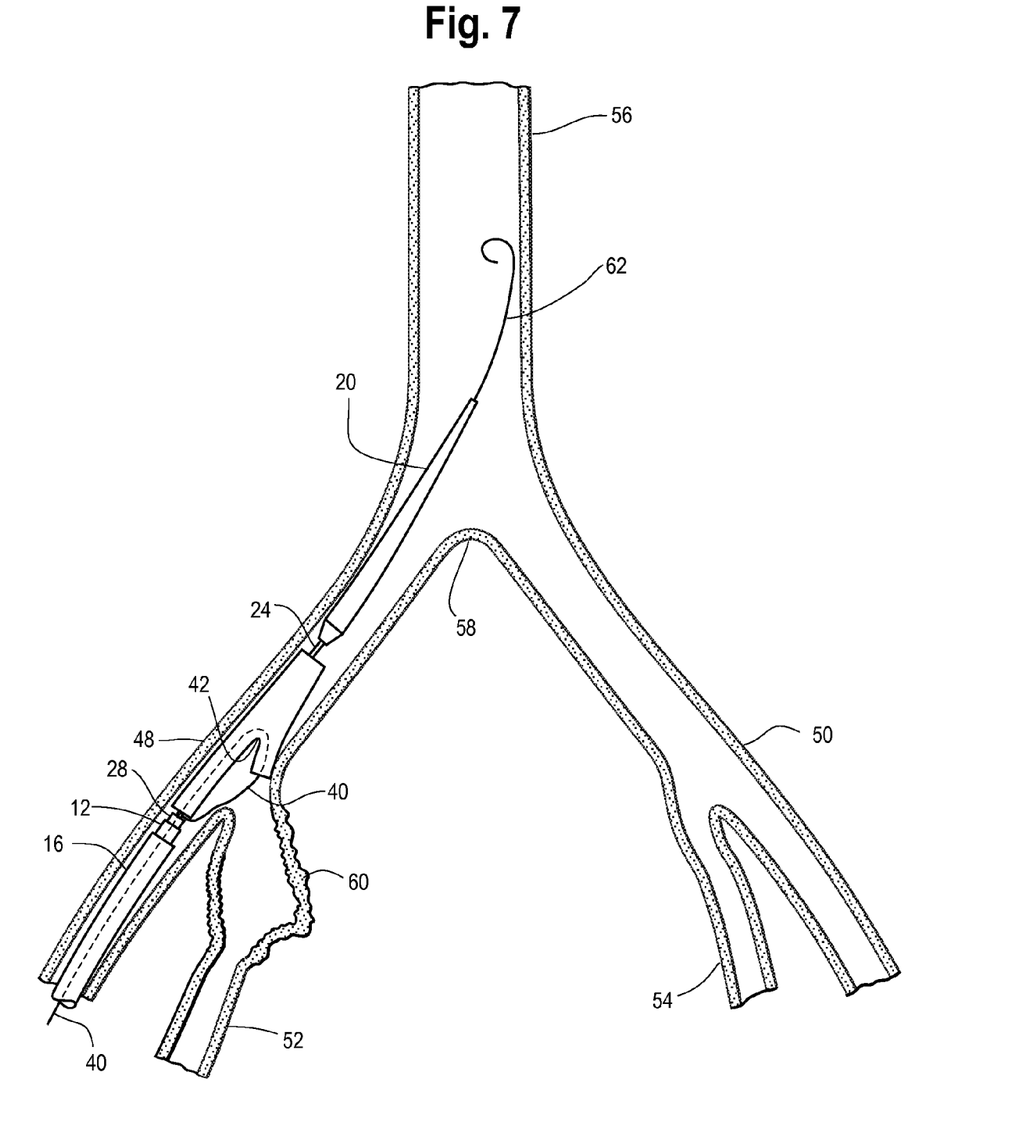

As shown in FIG. 7, the sheath 16 has been withdrawn (in a distal direction) to expose the branched stent graft 4 so that the sheath 16 is just distal of the proximal end portions 12, 28 of pusher catheter 10 and the auxiliary sheath 26, respectively. At this stage the branched stent graft 4 is partially unconstrained in that it has been freed from the confines of the sheath 16, but it is still retained by a retention mechanism at one or both of the proximal 3 and distal 5 ends of the stent graft. Accordingly, the stent graft 4 is not yet in a fully expanded condition within the lumen of the common iliac artery 48. It can be seen that the stent graft 4 carried on the device 2 is pre-loaded in one exemplary arrangement. More specifically, the device 2, with the stent graft 4 carried thereon, is pre-loaded as described above in connection with FIG. 2, but it is contemplated that the device can be pre-loaded in a variety of acceptable ways, including, but not limited to, the configuration described and shown in connection with FIG. 4 and/or a combined or modified version of one or more of the previously described configurations.

Figure 8:
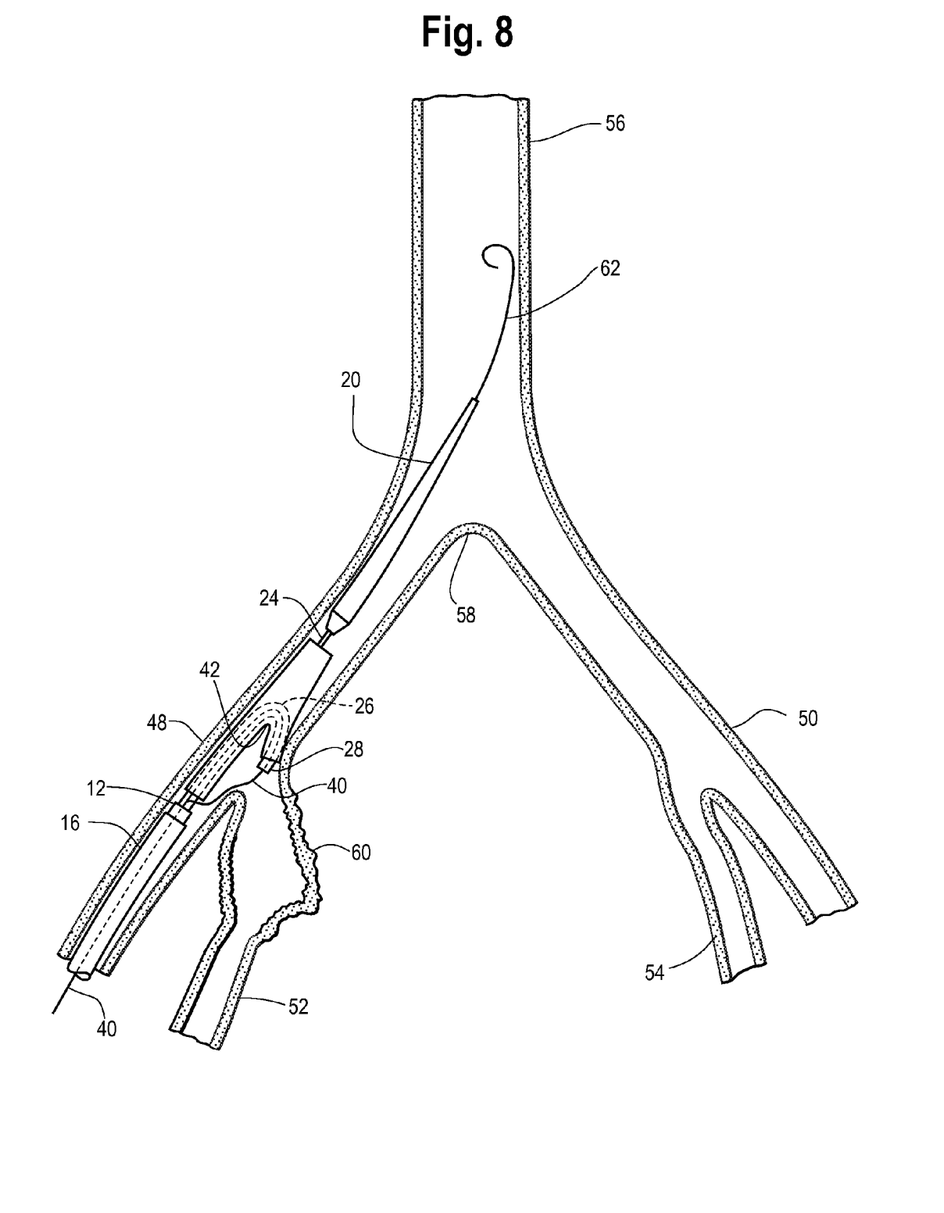

FIG. 8 shows the next stage of one example of a graft delivery and deployment sequence where the auxiliary sheath 26 is advanced over the auxiliary guide wire 40 so that the sheath enters the distal end 5 of the branched stent graft 4. The auxiliary sheath 40 is further advanced over the auxiliary wire 40, over stent bifurcation 42 and into the lumen of the side branch 36, until the tip 28 of the auxiliary sheath 26 extends out of the distal end of branch 48. (Or, alternatively, as described in connection with the embodiment shown in FIG. 5, the auxiliary sheath 26 would only be advanced a short distance into the proximal end portion 44 of the side branch lumen 36 until it abuts the interior lumen wall where the auxiliary wire 40 pierces and exits the branch lumen 36.) At this stage, the auxiliary guide wire 40 is still preferably in place such that it extends out of the distal end 46 of the side branch 34 and runs distally along the outside of the stent graft 4 through the common iliac artery 48 where the wire re-enters the lumen at proximal end 12 of pusher catheter 10 and extends back to the distal external manipulation section 8 of the device 2.

Figure 9:
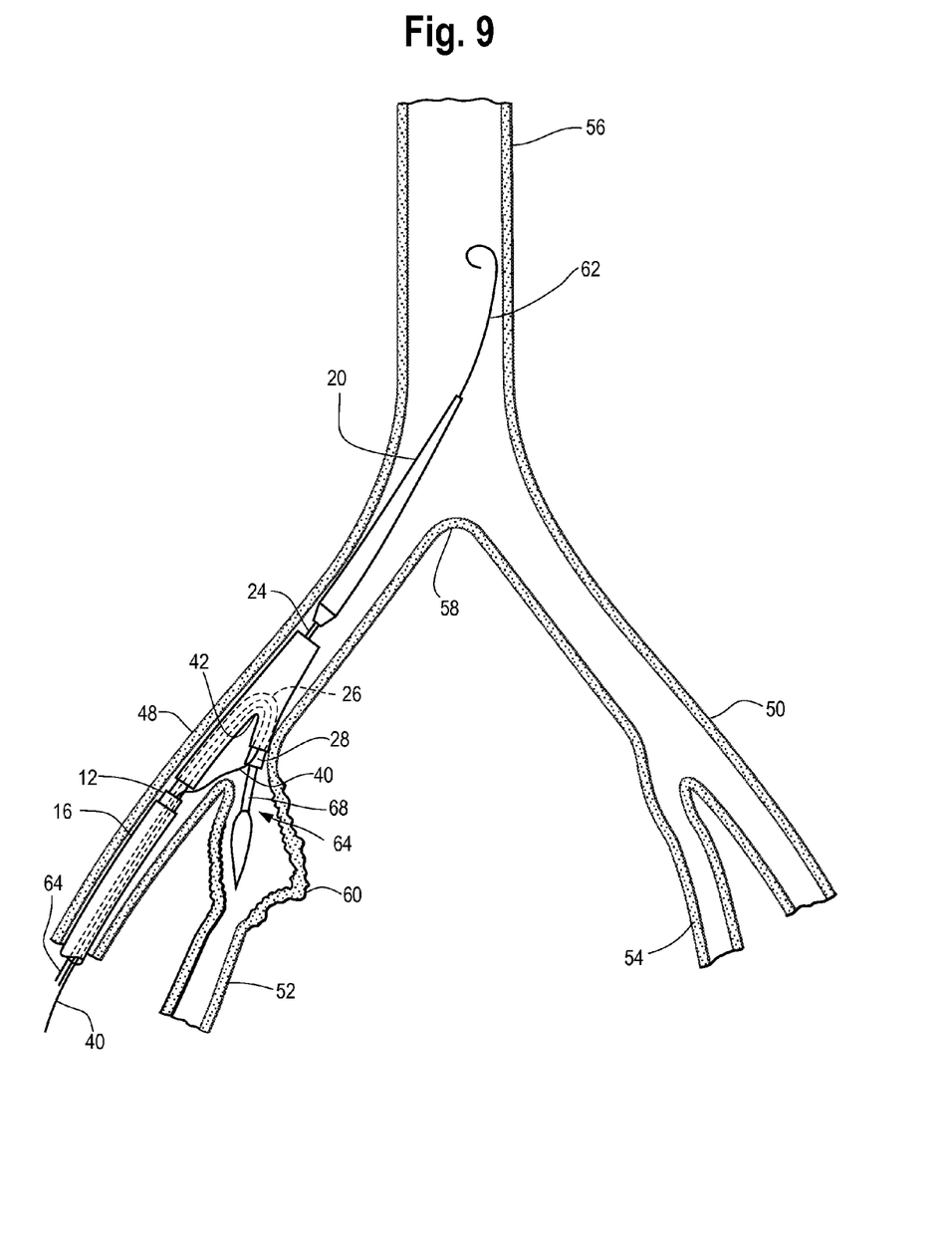
Figure 10:
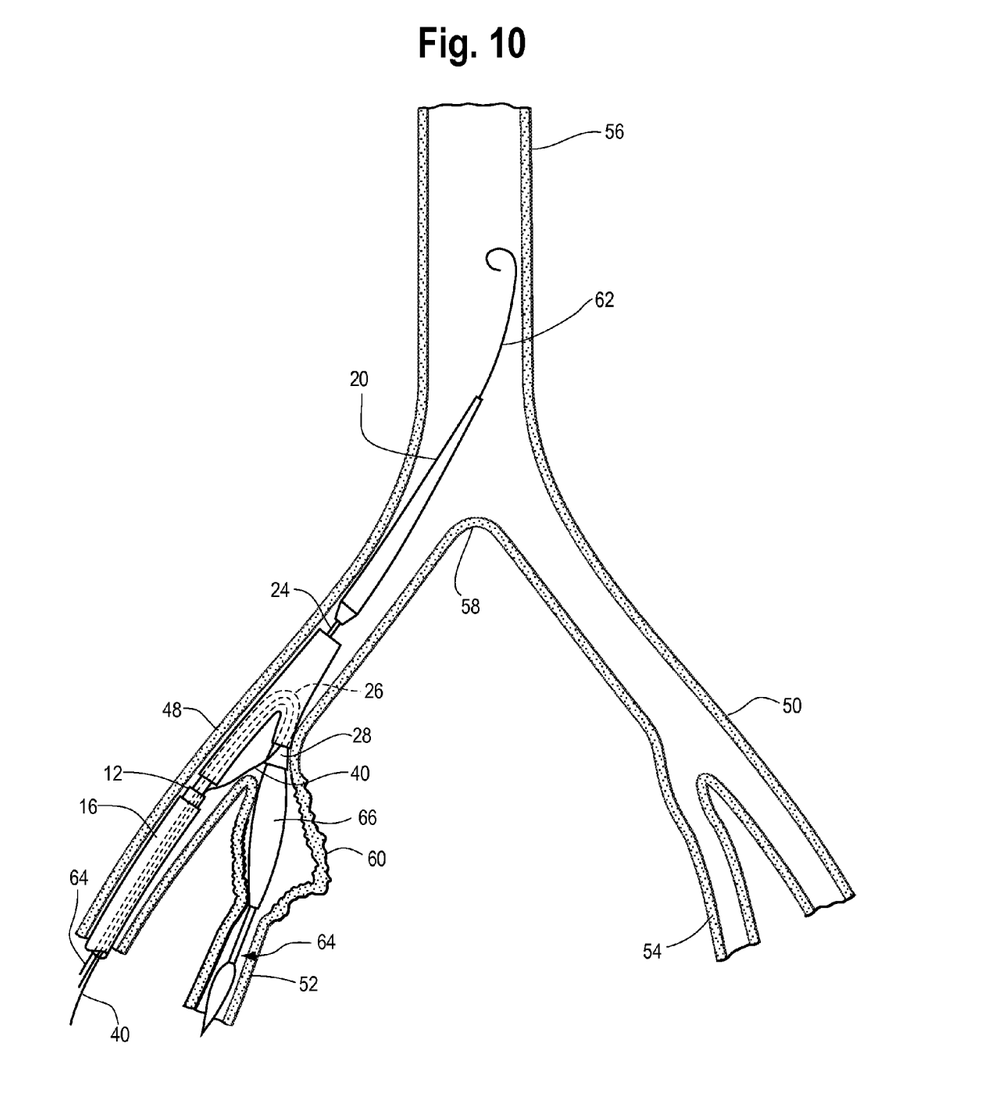
Figure 11:
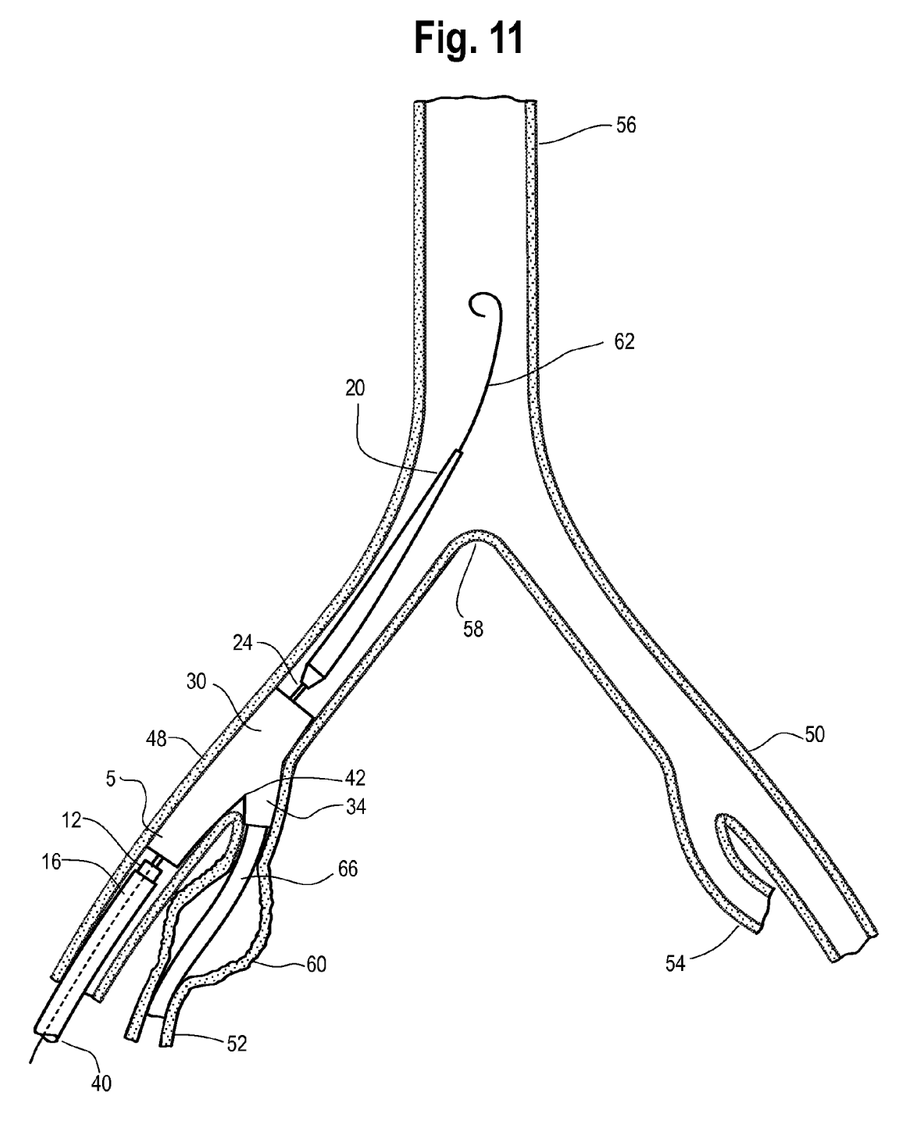

As shown in FIGS. 3 and 9, an additional stent graft or leg extension (ultimately intended for introduction and deployment in the internal iliac artery 52) is then preferably introduced into the internal iliac artery 52 using an ipsilateral approach. In one example, this may be accomplished by inserting a further delivery device 64 carrying a leg extension stent graft through the device 2. More particularly, as FIGS. 3 and 9 show, extension graft 66, covered by an appropriately sized sheath 68 (so that the graft 66 is not visible in FIGS. 3 and 9), is carried by further delivery device 64, and the device 64 is preferably tracked through the lumen of the auxiliary sheath 26 so that the further delivery device 64 extend towards and into the side branch lumen 36. As FIG. 9 shows, the graft 66, covered by sheath 68, extends distally beyond the tip 28 of the auxiliary sheath 26 and can be manipulated so that it enters the internal iliac artery 52. Preferably, as shown in FIGS. 10 and 11, extension graft 66 is positioned so that it extends both proximally and distally away from the location of aneurysm 60, therefore, spanning and bypassing the diseased portion of the vessel 52. At this stage, the further delivery device 64, extension sheath 68, and auxiliary sheath 26 can be withdrawn, preferably in a distal direction, from the common iliac artery 48, leaving the graft 66 in place in the internal iliac artery 52.

Further, as shown in FIGS. 10 and 11, the leg extension graft 66 preferably extends from the side branch 34 of the stent graft 4 into the internal iliac artery 52 and can be at least partially deployed in the internal iliac artery 52. In one example, as shown in FIG. 11, the release mechanism(s) at one or both ends of the stent graft 4, if present, can be released and the sheath 68 withdrawn from the leg extension graft 66 so that the branched stent graft 4 with the leg extension 66 is ready to be fully deployed in the common iliac artery 48 and internal iliac artery 52, respectively. The device 2 can also be withdrawn, if desired, although in some situations, it may be desirable to leave one or more components, such as pusher catheter 10 and/or the sheath 16 in position within the common iliac artery 48 so that further introduction and deployment of a stent graft into the aorta 56, such as a bifurcated stent graft, can be facilitated through the pusher 10 and/or sheath 16.

Figure 12:
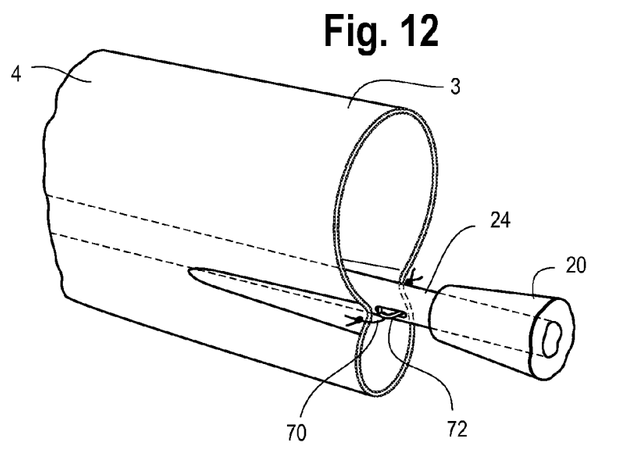
FIG. 12 is a perspective view of one example of proximal retention of a stent graft to a delivery device.
Figure 13:
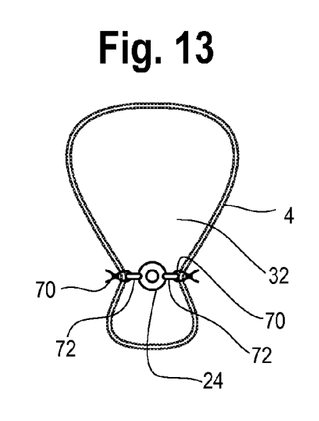
FIG. 13 is a cross-sectional view of the arrangement shown in FIG. 12.

Turning to FIG. 12, a perspective view of one suitable method of proximal retention of the stent graft 4 on the device 2 is shown, while FIG. 13 shows a cross sectional view of the arrangement shown in FIG. 12. The guide wire catheter 24 extends to the nose cone dilator 20 and, in one example, the proximal end portion 3 of the stent graft 4 is retained onto the guide wire catheter 24 just distal of the nose cone dilator 20. Retention may be by various means, and in one non-limiting example, may include one or more loops or stitches of suture material 70 which are engaged with a trigger wire 72 extending from an aperture in the guide wire catheter 24. However, it is also contemplated that other types and methods of proximal restraint may be used including various diameter reducing ties, fasteners or the like that are suitable for removably securing the stent graft 4 on the device 2.

The sutures 70 may be placed on one wall of the stent graft 4 or, alternatively, as shown in FIG. 13, may be placed on generally opposing walls of the tubular graft body 30. The sutures 70 may be placed in any suitable arrangement or location so that the graft 4 is removably secured to the device 2, and as FIGS. 12 and 13 show, they may be placed so that there is formed a smaller and larger lobe or fold of the stent graft at its proximal end 3. The proximal end 3 of the stent graft 4 may be released from this retention arrangement by releasing the one or more sutures 70, or any other type of proximal retention mechanism that may be used in combination with or in place of such sutures, during deployment of the graft within a vessel lumen.

Figure 14:
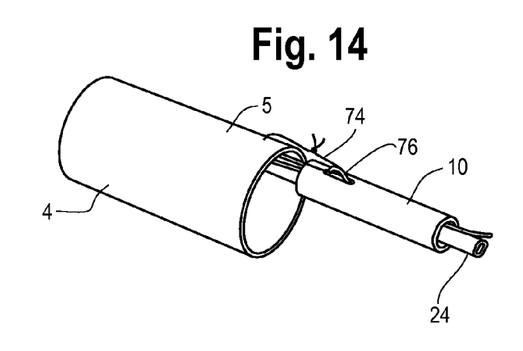
FIG. 14 is a perspective view of one example of distal retention of a stent graft to a delivery device.
Figure 15:
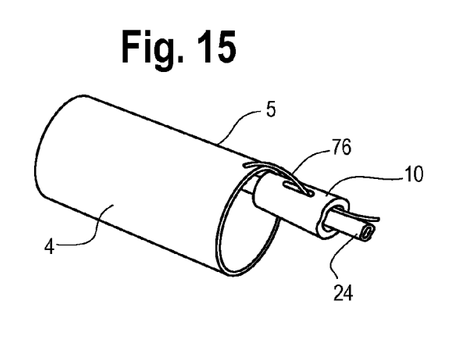
FIG. 15 is a perspective view of another example of distal retention of a stent graft to a delivery device.

FIG. 14 shows a perspective view of one suitable method of distal retention of the stent graft on the device 2. In this non-limiting example, the distal end 5 of the stent graft 4 may be retained onto the guide wire catheter 24 just proximal of the pusher catheter 10 by one or more sutures 74 which are engaged with a trigger wire 76 extending from an aperture in the guide wire catheter 24. However, like the proximal retention mechanism described above, it is also contemplated that other types and methods of distal restraint may be used including various diameter reducing ties, fasteners or the like that are suitable for removably securing the stent graft on the introducer. In another example shown in FIG. 15, the trigger wire 76 may pierce or be woven through the distal end 5 of the stent graft 4 directly, thus, retaining the graft against the guide wire catheter 24 until the trigger wire(s) 76 is removed. Removal of the trigger wire(s) 76 when desired or required will release the distal retention mechanism, thereby facilitating at least partial deployment of the distal end 5 of the stent graft 4 within a vessel lumen. Alternatively, one of the retention mechanisms may not be present and the stent graft 4 may be removably retained on the device 2 by the proximal end retention mechanism alone.

It is also contemplated that the leg extension graft 66 may also preferably include proximal and/or distal retention mechanisms that secure it to the further delivery device 64. Proximal and/or distal retention of graft 66 may include the same or similar retention mechanisms as those described above in connection with the retention of stent graft 4 on delivery device 2, such that graft 66 may be retained on further delivery device 64 in a manner similar to that shown in FIGS. 12-15. Of course, other types and methods of proximal and/or distal restraint of extension graft 66 may be used including various diameter reducing ties, fasteners or the like that are suitable for removably securing the extension graft 66 on the further delivery device 64. Proximal and/or distal retention of extension graft 66 may be in addition to or in combination with sheath 68 which also secures the graft 66 to further delivery device 64 and holds it in a radially inwardly compressed "pre-deployment" condition.

Once the proximal and/or distal retention mechanisms have been removed, the stent graft 4 and/or extension graft 66 may be radially expanded or deployed within the respective vessels. In one example, a "self-expanding" stent expands primarily based on its own expansive force without the need for further mechanical expansion. More particularly, a stent made of a shape-memory alloy such as Nitinol may allow the stent graft 4, 66 to return to a predetermined expanded configuration upon removal of a sheath (e.g., sheath 16 or 68) or other mechanism that maintains the stent graft in its compressed, pre-deployment configuration. In another example, stents made of materials such as stainless steel may expand on their own accord once released from constraints holding them in their compressed state. Alternatively, a stent graft 4, 66 may require further manipulation, mechanical or manual expansion, such as by balloon expansion by the user. In either case, it is contemplated that the stent graft 4, 66 may expand or deploy only partially within the vessel lumen after removal of one or both of the proximal and distal retention mechanisms, such that additional expansion of the stent graft may be desired or required, at which time the user may implement various known and acceptable techniques to fully deploy the stent graft 4, 66 in the main and/or branched vessel. Such fully deployed stent grafts 4 and 66 are illustrated in exemplary FIG. 11.

Thus, the pre-loaded delivery device described herein successfully facilitates the introduction, placement and deployment of a stent graft into one or more branched vessels using an ipsilateral approach, including, but not limited to a common iliac artery 48 and an internal iliac artery 52 extending therefrom, in order to treat and/or restore patency to one or both of such vessels.

Throughout this specification, unless the context requires otherwise, the words "comprise" and "include" and variations such as "comprising" and "including" will be understood to imply the inclusion of an item or group of items, but not the exclusion of any other item or group items.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A system for the delivery and deployment of an endovascular graft comprising:
   a. a delivery device comprising:
      i. a pusher catheter having a proximal end portion and a distal end portion and at least one lumen extending at least partially between the proximal and distal end portions;
      ii. a guide wire cannula having a proximal end portion and a distal end portion and extending longitudinally within the lumen of the pusher catheter;
   b. a stent graft carried on the delivery device, the stent graft comprising:
      i. a main tubular body of a biocompatible graft material having a proximal end and a distal end defining a main lumen therebetween,
      ii. a side branch extending from the main tubular body, the side branch having a lumen extending therethrough and being in fluid communication with the main lumen,
   c. an auxiliary guide wire extending proximally within the lumen of the pusher catheter and into the distal end of the main tubular body of the stent graft, the auxiliary guide wire further extending distally through at least a portion of the lumen of the side branch and through the lumen of the pusher catheter.

2. The system of claim 1 further comprising a second delivery device, the second delivery device comprising:
   a. a second guide wire cannula having a proximal end portion and a distal end portion and a lumen extending therebetween;
   b. a second stent graft carried on the proximal end portion of the second delivery device, the second stent graft comprising a tubular body of a biocompatible graft material defining a main lumen;
   c. a second sheath mounted coaxially over at least a portion of the second stent graft.

3. The system of claim 2 further comprising a second guide wire extending longitudinally within the lumen of the second guide wire cannula.

4. The system of claim 1 wherein the auxiliary guide wire extends through the entire longitudinal length of the side branch lumen.

5. The system of claim 1 wherein the side branch comprises a tubular body of biocompatible graft material having a proximal end portion and a distal end portion, and wherein the auxiliary guide wire pierces through the graft material of the side branch.

6. The system of claim 5 wherein the auxiliary guide wire extends distally outside of the lumen of the side branch and outside of the lumen of the main tubular body.

7. The system of claim 6 wherein the auxiliary guide wire enters the lumen of the pusher catheter at a location distal to the distal end of the main graft tubular body.

8. The system of claim 1 wherein the distally extending portion of the auxiliary guide wire enters the lumen of the pusher catheter at a location distal to the distal end of the main graft tubular body.

9. The system of claim 1 further comprising an auxiliary sheath comprising a proximal end portion and a distal end portion and a lumen extending therebetween, wherein the auxiliary sheath comprises a first position wherein the sheath proximal end portion is located distal to the distal end portion of the main graft tubular body.

10. The system of claim 1 further comprising an auxiliary sheath comprising a proximal end portion and a distal end portion and a lumen extending therebetween, wherein the auxiliary sheath comprises a second position wherein the sheath is advanced over the auxiliary guide wire such that the proximal end portion of the sheath extends at least partially into the lumen of the side branch.

11. The system of claim 10 wherein the second delivery device extends at least partially through the lumen of the auxiliary sheath.

12. The system of claim 11 wherein the second stent graft carried by the second delivery device is configured to be positioned within the internal iliac artery.

13. The system of claim 10 further comprising a second delivery device carrying a second stent graft, the second stent graft comprising a tubular body of a biocompatible graft material defining a main lumen.

14. The system of claim 13 wherein the second delivery device extends through the lumen of the auxiliary sheath when the auxiliary sheath is in the second position such that the second stent graft carried by the second delivery device is positioned within an internal iliac artery.

15. The system of claim 1 further comprising a sheath mounted coaxially over at least a portion of the pusher catheter.

16. The system of claim 15 wherein the sheath has an external diameter of about 5 Fr to about 7 Fr.

17. A system for the delivery and deployment of an endovascular graft comprising:
   a. a delivery device comprising:
      i. a pusher catheter having a proximal end portion and a distal end portion and a first, second and third lumen extending at least partially between the proximal and distal end portions;
      ii. an auxiliary sheath having a proximal end portion and a distal end portion extending longitudinally within the first lumen of the pusher catheter;
      iii. a guide wire cannula having a proximal end portion and a distal end portion and extending longitudinally within the second lumen of the pusher catheter;
   b. a stent graft carried on the delivery device, the stent graft comprising:
      i. a main tubular body of a biocompatible graft material having a proximal end and a distal end defining a main lumen therebetween,
      ii. a side branch extending from the main tubular body, the side branch having a lumen extending therethrough and being in fluid communication with the main lumen, whereby the stent graft is configured to be deployed into the vasculature of a patient with the main tubular body being located in the common iliac artery and the side branch being directed towards an internal iliac artery of the common iliac artery;
   c. an auxiliary guide wire extending proximally within the lumen of the auxiliary sheath and into the distal end of the main tubular body of the stent graft, the auxiliary guide wire further extending distally through at least a portion of the lumen of the side branch and through the third lumen of the pusher catheter.

18. The system of claim 17 further comprising a second delivery device, the second delivery device comprising:
   a. a second guide wire cannula having a proximal end portion and a distal end portion and a lumen extending therebetween;
   b. a second stent graft carried on the proximal end portion of the second delivery device, the second stent graft comprising a tubular body of a biocompatible graft material defining a main lumen, whereby the second stent graft is configured to be deployed into the internal iliac artery;
   c. a second sheath mounted coaxially over at least a portion of the second stent graft.

19. The system of claim 18 further comprising a second guide wire extending longitudinally within the lumen of the second guide wire cannula and configured for introduction into the internal iliac artery.

20. The system of claim 17 wherein the auxiliary guide wire extends through the entire longitudinal length of the side branch lumen.

21. The system of claim 17 wherein the side branch comprises a tubular body of biocompatible graft material having a proximal end portion and a distal end portion, and wherein the auxiliary guide wire pierces through the graft material at the proximal end portion of the side branch.

22. The system of claim 21 wherein the auxiliary guide wire extends distally outside of the lumen of the side branch and outside of the lumen of the main tubular body.

23. The system of claim 22 wherein the auxiliary guide wire enters the third lumen of the pusher catheter at a location distal to the distal end of the main graft tubular body.

24. The system of claim 17 wherein the distally extending portion of the auxiliary guide wire enters the third lumen of the pusher catheter at a location distal to the distal end of the main graft tubular body.

25. A method for treating a diseased vessel, the method comprising:
   a. introducing a first delivery device into a patient's vasculature comprising a common iliac artery, the delivery device comprising:
      i. a pusher catheter having a proximal end portion and a distal end portion and a lumen extending therebetween;
      ii. an auxiliary sheath having a proximal end portion and a distal end portion extending longitudinally within the lumen of the pusher catheter;
      iii. a first prosthesis carried on the first delivery device, the first prosthesis comprising a main tubular body of a biocompatible graft material having a proximal end portion and a distal end portion defining a main lumen therebetween and a side branch extending from the main tubular body, the side branch having a lumen extending therethrough and being in fluid communication with the main lumen, whereby the first prosthesis is configured to be deployed into the vasculature of a patient with the main tubular body being located in the common iliac artery and the side branch being directed towards an internal iliac artery of the common iliac artery;

iv. an auxiliary guide wire extending longitudinally in a proximal direction within the lumen of the auxiliary sheath and into the distal end of the main tubular body of the stent graft, the auxiliary guide wire further extending through at least a portion of the lumen of the side branch and extending longitudinally in a distal direction through the lumen of the pusher catheter;

b. at least partially deploying the first prosthesis in the common iliac artery;

c. introducing a second delivery device ipsilaterally though the lumen of the main tubular body and through the lumen of the side branch of the first prosthesis, the second delivery device carrying a second prosthesis thereon, the second prosthesis comprising a tubular body defining a lumen;

d. positioning the second prosthesis within the internal iliac artery;

e. at least partially deploying the second prosthesis in the internal iliac artery.

* * * * *